US008133874B2

(12) United States Patent
Wang et al.

(10) Patent No.: US 8,133,874 B2
(45) Date of Patent: Mar. 13, 2012

(54) OLIGONUCLEOTIDE OR ITS FUNCTIONAL HOMOLOGUE, A COMPOSITION COMPRISING THE SAME AND A METHOD OF TREATING B CELL NEOPLASM

(75) Inventors: Li-ying Wang, Beijing (CN); Mu-sheng Bao, Beijing (CN); Yong-li Yu, Beijing (CN)

(73) Assignee: Changchun Huapu Biotechnology Co., Ltd. (CN)

( * ) Notice: Subject to any disclaimer, the term of this patent is extended or adjusted under 35 U.S.C. 154(b) by 779 days.

(21) Appl. No.: 11/914,745

(22) PCT Filed: Feb. 13, 2006

(86) PCT No.: PCT/CN2006/000216
§ 371 (c)(1),
(2), (4) Date: Aug. 8, 2008

(87) PCT Pub. No.: WO2006/122464
PCT Pub. Date: Nov. 23, 2006

(65) Prior Publication Data
US 2009/0162279 A1   Jun. 25, 2009

(30) Foreign Application Priority Data
May 17, 2005   (CN) .......................... 2005 1 0069576

(51) Int. Cl.
*A61K 31/70* (2006.01)
*C07H 21/02* (2006.01)
*C07H 21/04* (2006.01)
*C12Q 1/68* (2006.01)

(52) U.S. Cl. ...... 514/44 A; 435/375; 435/377; 536/23.1; 536/24.1; 536/24.5

(58) Field of Classification Search .................. None
See application file for complete search history.

(56) References Cited

U.S. PATENT DOCUMENTS

| 6,896,885 B2 * | 5/2005 | Hanna ........................ 424/156.1 |
| 7,576,066 B2 * | 8/2009 | Krieg .......................... 514/44 R |

FOREIGN PATENT DOCUMENTS

| CN | 1526718 A | 9/2004 |
| CN | 1526719 A | 9/2004 |
| WO | WO 0122972 | 4/2001 |
| WO | WO 0197843 | 12/2001 |
| WO | WO 03030832 A2 | 4/2003 |
| WO | WO 03050241 A2 | 6/2003 |
| WO | WO 2004054657 | 7/2004 |
| WO | WO 2005014611 | 2/2005 |

OTHER PUBLICATIONS

Reid et al., Blood vol. 105(9):3641-3647, 2005.*
Decker et al Blood vol. 95(3):999-1006, Feb. 14, 2000.*
Banchereau, J. et al., Annual Rev. Immunology, "The CD40 Antigen and its Ligand", 1994, vol. 12; pp. 881-992.
Castle, B. E. et al., J. Immunology, "Regulation of Expression of the Ligand for CD40 on T Helper Lymphocytes", Aug. 15, 1993, vol. 151; pp. 1777-1788.
Chu, P. et al., PNAS, "Latent Sensitivity to Fas-mediated Apoptosis after CD40 Ligation may explain acivity of CD154 Gene Therapy in Chronic Lymphocytic leukemia", Mar. 19, 2002, vol. 99, No. 6; pp. 3854-3859.
Dalpke A.H. et al., "Immunostimulatory CpG-DNA Activates Murine Microglia." The Journal of Immunology, 2002, vol. 168; pp. 4854-4863.
Dicker, F. et al., Blood, "Fas-ligand (CD178) and TRAIL Synergistically Induce Apoptosis of CD40-Activated Chronic Lymphocytic Leukemia B Cells" Apr. 15, 2005, vol. 105, No. 8; pp. 3193-3198.
Dilloo, D. et al., Blood, "CD40 Ligand Induces an Antileukemia Immune Response in Vivo" 1997, vol. 90; pp. 1927-1933.
Hartmann, G., et al., "Delineation of CpG Phosphorothioate Oligodeoxynucleotide for Activating Primate Immune Response in Vitro and in Vivo." Journal of Immunology, 2000, vol. 164; pp. 1617-1624.
Kamstrup, S. et al., "Response of Porcine Peripheral Blood Mononuclear Cells to CpG-containing Oligodeoxynucleotides." Vet. Microbiol., Feb. 26, 2001, vol. 78, No. 4; pp. 352-362.
Khanna, R. et al., J. Immunology, "Cutting Edge: Engagement of CD40 Antigen with Soluble CD40 Ligand Up Regulates Peptide Transporter Expression and Restores Endogenous Processing Function in Burkitt's Lymphoma Cells", 1997, vol. 159; p. 5782-5785.
Kato, K. et al., J. Clin Invest., "Gene Transfer of CD40-Ligand Induces Autologous Immune Recognition of Chronic Lymphocytic Leukemia B Cells", Mar. 1998, vol. 101, No. 5; pp. 1133-1141.
Mocellin, S. et al., "Interleukin-10 and the Immune Response against Cancer: a Counterpoint." Journal of Leukocyte Biology. 2005, vol. 78; pp. 1043-1051.
Ranheim, E.A. et al. J. Exp Med, "Activated T Cells Induce Expressions of B7/BB1 on Normal or Leukemic B Cells through a CD40-dependent Signal", Apr. 1993 vol. 177; pp. 925-935. Takahashi, S., et al., Hum Gene Ther., "Autologous Antileukemic Immune Response Induced by Chronic Lymphocytic Leukemia B Cells Expressing the CD40 Ligand and Interleukin 2 Transgene", Apr. 10, 2001, vol. 12; pp. 659-670.
Takahashi, S. et al., Cancer Gene Ther., "Transgenic Expression of CD40L and interleukin-2 Induces an Autologous Antitumor Immune Response in Patients with non-Hodgkin's Lymphoma", 2001, vol. 8, No. 5; pp. 378-387.
Tokunaga, T. "Anti-tumor Activity of Deoxyribonucleic Acid Fraction from Mycobacterium bovis BCG.I. Isolation, Physicochemical Characterization and Anti-Tumor Activity" JNCI, 1984, vol. 72; p. 955.
Viet Hornung, et al., "Quantitative Expression of Toll-Like Receptor 1-10 mRNA in Cellular Subsets of Human Peripheral Blood Mononuclear Cells and Sensitivity to CpG Oligodeoxynucleotide." The Journal of Immunology, 2002, vol. 168; pp. 4531-4537.
von Bergwelt Baildon, M.S., et al., Blood, "Human Primary and Memory Cytotoxic T Lymphocyte Response are Efficiently Induced by means of CD40-activated B cells as Antigens-presenting cells: Potential for clinical application", May 1, 2002, vol. 99, No. 9; pp. 3319-3325.
Weiner, G. J. "The Immunobiology and Clinical Potential of Immunostimulatory CpG Oligodeoxynucleotides" J. Leukoc Biol., Oct. 2000, vol. 68; pp. 455-463.
Wierda, W. G., et al., Blood, "CD40-ligand (CD154) Gene Therapy for Crhonic Lymphocytic Leukemia", Nov. 1, 2000, vol. 96; pp. 2917-2924.

(Continued)

Primary Examiner — Sean McGarry
(74) Attorney, Agent, or Firm — Morgan, Lewis & Bockius LLP (57) ABSTRACT

The invention provides an oligonucleotide with a sequence of SEQ ID NO: 1 or its functional homolgue, a composition comprising the same and a method for treating B cell neoplasm by using the oligonucleotide or its functional homologue or the composition comprising the oligonucleotide. The oligonucleotide induces the apoptosis of B cell neoplastic cells, up-regulates CD40 on B cell neoplastic cells and stimulates the production of IL-10 from B cell neoplastic cells.

15 Claims, 4 Drawing Sheets

OTHER PUBLICATIONS

Yellin, M. J., et al., J. Immunol, "T Lymphocyte T Cell-B Cell-Activating Molecule/CD4O-L Molecules Induce Normal B Cells or Chronic Lymphocytic Leukemia B Cells to Express CD80 (87/BB-1) and Enhance Their Costimulatory Activity", 1994, vol. 153; pp. 666-674.

D'Amico, G. et al., "CD40 Activation of BCP-ALL cells Generated IL-10 Producing, IL-12-defective APCs that Induce Allogenetic T-cell Anergy", Immunobiology Blood, vol. 104, No. 3, Aug. 1, 2004.

Decker, et al. "Immunostimulatory CpG-oligonucleotides cause Proliferation Cytokine production, and Immunogenic Phenotype in Chronic Lymphocytic Leukemia B cells." Blood vol. 95(3): 999-1006, 2000.

Decker, et al., "Sensitization of B-Cell Chronic Lymphocytic Leukemia Cells to Recombinant Immunotoxin by Immunostimulatory Phosphorothioate Oligodeoxynucleotides" Blood, vol. 99, No. 4, pp. 1320-1326, Feb. 15, 2002.

Li, J., et al. "CpG in the Immunothereapy of B Cell Lymphoma in an Animal Model", Journal of Immunotherapy, vol. 27, No. 6, p. S60, Nov. 2004.

Jahrsdörder, B., et al., "B-Cell Lymphomas Differ in their Responsiveness to CpG Oligodeoxynucleotides." Clinical Cancer Research, vol. II, pp. 1490-1499, Feb. 15, 2005.

Reid, G.S., et al., "CpG Stimulation of Precursor B-lineage Acute Lymphoblastic Leukemia Induces a Distinct Change in Costimulatory Molecule Expression and Shifts Allogeneic T cells towards a Th 1 Response", Blood, May 1, 2005, vol. 105, No. 9; pp. 3641-3646.

Warren, T. L., et al. "Synergism between Cytosine-Guanine Oligodeoxynucleotides and Monoclonal Antibody in the Treatment of Lymphoma." Seminars in Oncology, vol. 29, No. I, Suppl. 2; pp. 93-97, Feb. 2002.

* cited by examiner

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Oligo-2

<400> SEQUENCE: 1
tcgtcgacgt cgttcgttct c                                              21

<210> SEQ ID NO 2
<211> LENGTH: 24
<212> TYPE: DNA
<213> ORGANISM: Artificial Sequence
<220> FEATURE:
<223> OTHER INFORMATION: control oligonucleotide 2006

<400> SEQUENCE: 2
tcgtcgtttt gtcgttttgt cgtt                                           24

<210> SEQ ID NO 3
<211> LENGTH: 20
<212> TYPE: DNA
<213> ORGANISM: Artificial Sequence
<220> FEATURE:
<223> OTHER INFORMATION: control oligonucleotide 2216
```

```
<400> SEQUENCE: 3
gggggacgat cgtcggggg                                              20
```

OLIGONUCLEOTIDE OR ITS FUNCTIONAL HOMOLOGUE, A COMPOSITION COMPRISING THE SAME AND A METHOD OF TREATING B CELL NEOPLASM

CROSS-REFERENCES TO RELATED APPLICATIONS

The present application is a U.S. National Phase of PCT Patent Application No. PCT/CN06/000216 filed Feb. 13, 2006 and claims priority to Chinese Patent Application 200510069576.4 filed on May 17, 2005, each of which is incorporated herein by reference in its entirety for all purposes.

TECHNICAL FIELD

The present invention provides a oligonucleotide with a sequence as shown in SEQ ID NO:1, or its functional homologue, a composition comprising the same and a method for treating B-cell neoplasm using the oligonucleotide by inducing apoptosis of B cell neoplastic cells, up-regulating CD40 on B cell neoplastic cells and by stimulating B cell neoplastic cells to produce IL-10. The oligonucleotide or its functional homologue can be used alone or in combination with chemotherapeutics, immunotherapeutics and radiation to treat B cell neoplasm.

BACKGROUND

Based WHO classification system (American Journal of Surgical Pathology, 1997, 21(1): 114-121), lymphoid malignancies are grouped into three major classes: B-cell neoplasm, T-cell/natural killer (NK)-cell neoplasm and Hodgkin's lymphomas.

The B-cell neoplasm is further divided into two groups: precursor B-cell neoplasm and peripheral B-cell neoplasm. Precursor B-cell neoplasm includes precursor B-acute lymphoblastic leukemia (B cell-acute lymphoblastic leukemia, B-ALL)/lymphoblastic lymphoma (LBL). Peripheral B-cell neoplasm includes B-cell chronic lymphocytic leukemia (B-CLL), small lymphocytic lymphoma, B-cell prolymphocytic leukemia, lympho plasmacytic lymphoma/immunocytoma, Mantle cell lymphoma, Follicular lymphoma, cutaneous follicular lymphoma, extranodal marginal zone B-cell lymphoma of MALT type, nodal marginal zone B-cell lymphoma (+/−monocytoid B-cells), splenic marginal zone lymphoma (+/−villous lymphocytes), hairy cell leukemia, plasmacytoma/plasma cell myeloma, diffuse large B-cell lymphoma, mediastinal (thymic) large B cell lymphoma, intravascular large B-cell lymphoma, primary effusion lymphoma and Burkift's lymphoma.

B-cell chronic lymphocytic leukemia (B-CLL) and B cell-acute lymphoblastic/lymphocytic leukemia (B-ALL) are two types of B cell leukemia. The B-CLL cells express CD19, CD5 and CD23 (Nicholas Chiorazzi, M.D., et al. N Engl. J Med 2005; 352:804-15). The B-ALL cells express CD19+ CD10+ markers.

Small lymphocytic lymphoma is a B cell neoplasm. The monoclonal population of B cells in small lymphocytic lymphoma expresses CD19, CD5 and CD23 (Catherine Thieblemont, et al. Blood. 2004; 103:2727-2737).

Depending on the B-cell neoplasm diagnosed, current treatment options are chemotherapy, radiotherapy and immunotherapy.

CD40, expressed on the cell surface of normal B lymphocytes and dentritic cells, is a member of tumor necrosis factor receptor (TNFR) family. CD40L (CD154), expressed on T lymohocytes, is a member of tumor necrosis factor family (Castle B E, et al. J Immunol 1993; 151: 1777-1788). Interaction of CD40L and CD40 promotes the proliferation, differentiation and antigen presentation of B lymphocytes, dendritic cells and monocytes (Ranheim E A, et al. J Exp Med 1993; 177: 925-935; Yellin M J, et al. J Immunol 1994; 153: 666-674; Banchereau J, et al. Anhu Rev Immunol 1994; 12: 881-922; M. von Bergwelt-Baildon M S, et al. Blood 2002; 99: 3319-3325).

CD40 also expresses on the B cell neoplastic cells. It has been demonstrated that enhancing the CD40 expression promotes the apoptosis of B cell neoplastic cells (Peter Chu, et al. PNAS, March 19, 2002, vol. 99, no: 6 3854-3859; Frank Dicker, et al. BLOOD, 15 Apr. 2005 Volume 105, Number 8: 3193-3198).

Both in vitro and in vivo experiments indicated that stimulation and up-regulation of CD40 induced growth inhibition of B-cell neoplastic cells (Funakoshi et al., Blood 83: 2787-2794,1994; Murphy et al., Blood 86: 1946-1953,1995; Eliopoulos, A. G., et al. 1996. Oncogene 13:2243; Hirano, A., et al. 1999. Blood 93:2999; Tong, A. W., M et al. 2001.Clin. Cancer Res. 7:691).

Promoting CD40 expression on B cell neoplastic cells was reported to enhance the antigenicity of B cell neoplastic cells and consequently fostered the generation of cytotoxic T lymphocyte (CTL) specific to the cells. The CTL can efficiently kill B cell neoplastic cells (Dilloo D, et al. Blood. 1997; 90:1927-1933; Kato K, et al. J Clin Invest. 1998; 101:1133-1141; Wierda W G, et al. Blood. 2000; 96:2917-2924; Takahashi S, et al. Hum Gene Ther. 2001; 12:659-670; Takahashi S, et al. Cancer Gene Ther. 2001; 8:378-387). In the presence of CD40L, CD40 expressing B cell chronic lymphocytic leukemia cells can be killed by CD4 cytotoxic T lymphocytes (Frank Dicker, et al. Blood, 15 Apr. 2005 Vol 105, Num 8: 3193-3198). Interaction of D40L and CD40 on cells of Burkett's lymphoma could promote the cell to present tumor antigens to specific CTLs (Khanna, R. et al. 1997. J. Immunol. 159:5782). In vivo experiments and clinical trials also demonstrated that activation of CD40 could enhance the immunogenicity of B cell chronic lymphocytic leukemia (B-CLL) cell and consequently induce the generation of CTLs specific to the cells (Kato, K., et al. 1998. J. Clin. Invest. 101:1133; Wierda, W. G., et al. 2000. Blood 96: 2917).

Together, these data indicate that enhancing CD40 expression on B cell neoplastic cells can stimulate the anti-tumor immunity against B cell neoplasm. The anti-tumor immunity includes but not limits to the following:
1. promoting the apoptosis of B cell neoplastic cells;
2. inhibiting the growth of B cell neoplastic cells;
3. enhancing the immunogenicity of B cell neoplastic cells and therefore fostering the generation of CTLs specific to the cells.

Interleukin-10 (IL-10) is a homodimer cytokine produced by certain T cells, monocytes, macrophages and some of neoplastic cells developed from B cells, T cells or NK cells (Kitabayashi et al., 1995; Masood et al., 1995; Sjoberg et al., 1996; Beatty et al., 1997; Boulland et al., 1998; Jones et al., 1999). IL-10 activity is mediated by its specific cell surface receptor. The receptor expresses on antigen-presenting cells, lymphocytes and also B-cell chronic lymphocytic leukemia (B-CLL) cells. It was found that addition of exogenous IL-10 inhibited the proliferation of B-CLL cells freshly isolated from patients (Jesper Jurlander, Chun-Fai Lai, Jimmy Tan, et al. Characterization of interleukin-10 receptor expression on B-cell chronic lymphocytic leukemia cells. Blood, Vol 89, No 11 (June 1), 1997: pp 4146-4152). IL-10 was also reported to inhibit the proliferation of B-CLL cells and enhance the apoptosis of B-CLL cells (Anne-Catherine Fluckiger, Isabelle Durand, and Jacques Banchereau. Interleukin 10 Induces Apoptotic Cell Death of B-Chronic Lymphocytic Leukemia Cells. J. Exp. Med. Volume 179 January 1994 91-99). Immunostimulating anticancer properties of IL-10 have been discussed in a review from which it is speculated that IL-10 over-expression within the tumor microenvironment may catalyze cancer immune rejection (Simone Mocellin, Francesco M. Marincola and Howard A. Young. Interleukin-10 and the immune response against cancer: a counterpoint. Journal of Leukocyte Biology. 2005; 78:1043-1051).

In the present invention, we provide an oligonucleotide and a method for treating B cell neoplasm by using the oligonucleotide of the present invention. The oligonucleotide induces the apoptosis of B cell neoplastic cells, promotes CD40 expression on B cell neoplastic cells and stimulates the B cell neoplastic cells to produce IL-10, which all contributes to the treatment of a B cell neoplasm.

SUMMARY OF THE INVENTION

In the first embodiment, the present invention provides a oligonucleotide with a sequence of 5'-TCGTCGACGTCGT-TCGTTCTC-3' (designed as Oligo-2 or indicated SEQ ID NO:1), or its functional homologue. The Oligonucleotide or its functional homologue can have a phosphate backbone modification that is a phosphorothioate or phosphorodithioate modification partial or complete. The oligonucleotide or its functional homologue may have chemical modifications or have substitutions with rare bases. The oligonucleotide or its functional homologue can be a functional part of any other oligonucleotide or DNA fragment or be cloned into a plasmid, bacterial vector, viral vector or DNA vaccine respectively. The oligonucleotide with the sequence of SEQ ID NO:1 can be modified by adding one or more bases (preferable 1 to 10 based) to its each end or by changing bases in it. Those skilled in the art can determine to use the oligonucleotide with the sequence of SEQ ID NO:1 or its functional homologue, or the DNA fragment, single stranded or double stranded, comprising one or more copies of the oligonucleotide with the sequence (SEQ ID NO:1) to achieve the object of the present invention based on the well-knowledge in the art and the teaching of the present invention.

In the second embodiment, the present invention provides a method for treatment of B cell neoplasm using the oligonucleotide or its functional homologue of the present invention or the composition comprising the same in a subject. The subject is a human or animal. The B cell neoplasm includes but not limited to B cell leukemia, B cell lymphoma and myeloma.

In the third embodiment, the present invention provides a method for treating B cell neoplasm using the oligonucleotide or its functional homologue of the present invention or the composition comprising the same by inducing the apoptosis of B cell neoplastic cells.

In the fourth embodiment, the present invention provides a method for treating B cell neoplasm using the oligonucleotide or its functional homologue of the present invention or the composition comprising the same by up-regulating CD40 on B-cell neoplastic cells.

In the fifth embodiment, the present invention provides a method for treating B cell neoplasm using the oligonucleotide or its functional homologue of the present invention or the composition comprising the same by stimulating B-cell neoplastic cells to produce IL-10.

In another embodiment, the present invention provides a composition comprising therapeutically effective amount of the oligonucleotide or its functional homologue of present invention alone or in/with one more pharmaceutically acceptable carriers. The composition can be administered through enteral, parenteral and topical administration or by inhalation.

In yet another embodiment, the present invention provides a method for the treatment of B cell neoplasm, comprising administering a therapeutically effective amount of the oligonucleotide or its functional homologue of the present invention or the composition comprising the same and at least one of anti-B cell neoplasm agents including chemotherapeutics, immunotherapeutics and the agents used in radiotherapy.

BRIEF DESCRIPTION OF THE DRAWINGS

B-CLL cells were cultured in 10% human AB serum medium with or without various amount of Oligo-2. On day 7, the cells were stained with TMRE. The viable B-CLL cell number was calculated for TMRE-positiVe cell percentage.

The B-CLL cells were incubated with or without Oligo 2 for 7 days and then stained with FITC-CD40 antibody for analysis of CD40 expression using flow cytometry. The expression level was indicated with MFI number.

B-ALL cells were incubated with or without Oligo-2. On day 3, 5 and 7 of the incubation, the cells were stained with TMRE, followed by flow cytometry analysis. The viable B-ALL cell number was calculated for TMRE-positive cell percentage.

B-ALL cells were cultured with or without 1 µg/ml Oligo-2. On day 3, 5 and 7 of the culture, the cells were stained with FITC-labeled anti-CD40 mAb for analysis of CD40 expression using flow cytometry. The expression level was indicated with MFI number.

The B-CLL cells were cultured with or without Oligo-2 in a serum-free medium. The supernatants were collected at the indicated time point and assessed for IL-10 using an ELISA kit.

The normal human PBMCs were cultured with Oligo-2, 2216 or 2006 for 36 h and then incorporated with [$^3$H] thymidine for determining the proliferation of the cells, respectively. The five blood samples were analyzed. The proliferation of cells was expressed as SI.

DETAILED DESCRIPTION OF THE INVENTION

Definitions

In this invention, the following terms shall have the meanings below:

An "oligonucleotide" means multiple nucleotides (i.e. molecules comprising a sugar (e.g. deoxyribose) linked to a phosphate group and to an exchangeable organic base). There are four organic bases cytosine (C), thymine (T), adenine (A) and guanine (G). The oligonucleotide can be synthesized by an automated oligonucleotide synthesizer available in the market or be prepared from existing nucleic acid sequences using known techniques.

A "back bone modification" of oligonucleotide shall mean that an oligonucleotide has a phosphorothioate modified phosphate backbone (i.e. at least one of the oxygens of the phosphate is replaced by sulfur) or other modified backbone. A "chemical modification" of oligonucleotide shall mean the modification by utilizing the active groups of the nucleotide or creating nucleotide analogues. The modifications can occur either during or after synthesis of the oligonucleotide. During the synthesis, modified bases (including but not limited to Thymidine analogues) can be incorporated internally or on the 5' end. After the synthesis, the modification can be carried out using the active groups (via an amino modifier, via the 3' or 5' hydroxyl groups, or via the phosphate group).

A "B cell neoplasm" shall mean diseases developed from the abnormal proliferation of the cells of B lymphocyte lineage. The B cell neoplasm can be grouped into B cell leukemia, B cell lymphoma and myeloma (plasmacytoma/plasma cell myeloma). B cell leukemia includes B-cell chronic lymphocytic leukemia (B-CLL), precursor B-acute lymphoblastic leukemia (B cell acute lymphocytic leukemia, B-ALL), B-cell prolymphocytic leukemia and hairy cell leukemia. B cell lymphoma includes small lymphocytic lymphoma, lympho plasmacytic lymphoma/immunocytoma, Mantle cell lymphoma, Follicular lymphoma, cutaneous follicular lymphoma, extranodal marginal zone B-cell lymphoma of MALT type, nodal marginal zone B-cell lymphoma (+/−monocytoid B-cells), splenic marginal zone lymphoma (+/−villous lymphocytes), diffuse large B-cell lymphoma, mediastinal (thymic) large B cell lymphoma, intravascular large B-cell lymphoma, primary effusion lymphoma and Burkitt's lymphoma. A "subject" shall mean a mammal including but not limited to human, monkey, dog, cat, horse, cow, pig, goat, sheep, mouse and rat. The oligonucleotide of the invention can be administered to a subject with B cell neoplasm.

An "anti-B cell neoplasm agent" shall mean an agent used to treat B cell neoplasm in a subject. The agent includes the oligonucleotide of this invention, chemotherapeutics, immunotherapeutics and the agents used in radiotherapy. The oligonucleotide of the invention can be administered prior to, along with or after administration of one or more other anti-B cell neoplasm agents to achieve synergistic effect in treating a B cell neoplasm.

The "chemotherapeutics" shall mean the chemotherapeutics that treat B cell neoplasm in combination with the oligonucleotide of the invention. The oligonucleotide of this invention can be used with one or more chemotherapeutics in the treatment of B cell neoplasm. The chemotherapeutics include, but not limited to alkylating agents such as cyclophosphamide or chlorambucil, vinca alkaloids (e.g., vincristine and vinblastine), procarbazine, methotrexate, prednisone, anthracycline, L-asparaginase, purine analogs (e.g., fludarabine monophosphate, 2-chlorodeoxyadenosine and pentostatin, cytosine, arabinoside, cisplatin, etoposide and ifosfamide. The oligonucleotide of this invention can also be used with one or more chemotherapeutic combinations in the chemotherapy. The combinations include, but not limited to CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin), MACOP-B (methotrexate, doxorubicin, cyclophosphamide, vincristine, fixed dose prednisone, bleomycin and leucovorin), IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP (B) (cyclophosphamide, etoposide, procarbazine, prednisone and bleomycin), CAMP (lomustine, mitoxantrone, cytarabine and prednisone), CHOP plus bleomycin, methotrexate, procarbazine, nitrogen mustard, cytosine arabinoside and etoposide. MOPP (mechlethamine (nitrogen mustard), vincristine (Oncovin), procarbazine and prednisone), ABVD (e.g., adriamycin, bleomycin, vinblastine and dacarbazine), ChIVPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) and CAP (cyclophosphamide, doxorubicin and prednisone).

The "immunotherapeutics" shall mean the immunotherapeutics that treat B cell neoplasm in combination with the oligonucleotide of the invention. The oligonucleotide of this invention can be used with one or more immunotherapeutics in the treatment of B cell neoplasm. The immunotherapeutics include, but not limited to anti-CD20 antibodies. The CD20 antibody includes immunoglobulins and its fragments that are specifically reactive with a CD20 protein on cell surface of B cell neoplastic cells. CD20 antibodies can be polyclonal and monoclonal antibodies, chimeric antibodies, bi-specific antibodies and humanized antibodies. A "CD20" is a B-cell membrane protein (Tedder et al., Immunology Today 15: 450-454 (1994)) and is expressed on both normal and neoplastic B-cell (John C. Byrd, et al. J Clin Oncol 2001; 19: 2165-2170; Huhn D, et al. Blood 2001, 98: 1326-1331).

A "pharmaceutically acceptable carrier" denotes one or more solid or liquid filler, diluents or encapsulating substances that are suitable for administering the oligonucleotide of the invention to a subject. The carrier can be organic, inorganic, natural or synthetic. The carrier includes any and all solutions, diluents, solvents, dispersion media, liposome, emulsions, coatings, antibacterial and anti-fungal agents, isotonic and absorption delaying agents, and any other carrier suitable for administering the oligonucleotide of the invention and their use is well known in the art.

The "therapeutically effective amount" of the oligonucleotide of the invention shall refer to a dose used to achieve a desired result of treating B cell neoplasm in a subject. The dose can be determined by standard techniques well known to those skilled in the art and can vary depending the factors including, but not limited to the size or/and overall health of the subject or the severity of the disease. Introduction of the oligonucleotide of the invention can be carried out as a single treatment or over a series of treatments. Subject doses of the oligonucleotide of the invention for the administration range from about 1 μg to 100 mg per administration. However, doses for the treatment of B cell neoplasm may be used in a range of 10 to 1,000 times higher than the doses described above. The dosage regimen can be adjusted to provide the optimum therapeutic effect by those skilled in the art.

The "route" of administering the oligonucleotide of the invention shall mean the enteral, parenteral and topical administration or inhalation. The term "enteral" as used herein includes oral, gastric, intestinal and rectal administration. The term "parenteral" includes intravenous, intraperitoneal, intramuscular, subcutaneous, rectal or vaginal administration. The term "topical" denotes the application of the oligonucleotide externally to the epidermis, to the buccal cavity and into the ear, eye and nose.

A "pharmaceutical composition" shall mean the composition comprising an therapeutically effective amount of the oligonucleotide of the invention with or without a pharmaceutically acceptable carrier. The composition includes but not limited to aqueous or saline solutions, particles, aerosols, pellets, granules, powders, tablets, coated tablets, (micro) capsules, suppositories, syrups, emulsions, suspensions, creams, drops and other pharmaceutical compositions suitable for use in a variety of drug delivery systems. The compositions are suitable for injection, buccal, oral, rectal and vaginal use, inhalation and application in depot. In all cases, the composition must be sterile and stable under the conditions of manufacture and storage and preserved against the microbial contamination. For injection, the composition will include aqueous solutions or dispersions and powders for the extemporaneous preparation of injectable solutions or dispersion. "Powder" in this invention refers to a composition that contains finely dispersed solid particles containing the oligonucleotide of the invention. The powder may be formulated with other pharmaceutically accepted carriers (e.g., water, PBS, saline and other pharmaceutically accepted buffers) before use. The solutions can be prepared by incorporating the oligonucleotide in one or more appropriate solvents and other required ingredients. Dispersions can be prepared by incorporating the oligonucleotide into a vehicle, which contains a dispersion medium (e.g., glycerol, liquid polyethylene glycols and oils) and the other required ingredients. For oral administration, the composition will be formulated with edible carriers to form tablets, pills, dragees, capsules, liquids, gels, syrups, slurries, suspensions and the like. For buccal administration, the composition will be tablets or lozenges in conventional manner. For inhalation, the composition will be an aerosol spray from pressurized packs or a nebulizer or a dry powder and can be selected by one of skill in the art. The oligonucleotide may also be formulated as pharmaceutical acceptable compositions for rectal or vaginal applications and for depot application. The oligonucleotide of the invention in the composition can be used alone or in combination with one or more other agents including not limited to chemotherapeutics, immunotherapeutics and a ligand recognized by a specific receptor or molecule of target cell. The oligonucleotide of the invention in combination with another agent can be separate compositions and used as the following: (1) the oligonucleotide is mixed with a second agent before administration; (2) the oligonucleotide and a second agent are administered to a subject at different times; (3) the oligonucleotide and a second agent are administered to different sites of a subject. In addition, the composition may contain plasmid, bacterial vectors, viral vectors and nucleic acid vaccines carrying the sequence of the oligonucleotide of the invention.

EXAMPLES

The following examples are illustrative, and should not be viewed as limiting the scope of the present invention. Reasonable variations, such as those occur to reasonable artisan, can be made herein without departing from the scope of the present invention.

Example 1

Synthesis of the Oligonucleotide

A oligonucleotide with a sequence of 5'-TCGTCGACGTCGTTCGTTCTC-3' (designed as Oligo-2, SEQ ID NO:1) has been designed and synthesized. To analyze the functions of the Oligo-2, two control oligonucleotides of 2006 with the sequence of 5'-tcgtcgttttgtcgttttgtcgtt-3' (SEQ ID NO:2) and 2216 with the sequence of 5'-gggggacgatcgtcgggggg-3' (SEQ ID NO:3) were also synthesized. Three of the oligonucleotide were synthesized in Sangon Biotech Company (Shanghai, China), tested for endotoxin by using the Limulus amebocyte lysate assay (Associates of Cape Cod, Inc) and manipulated in pyrogen-free reagents. 2006 ( J Immunol 2000: 164: 1617) is a well studied oligonucleotide that strongly activates normal B cells. 2216 (Eur J Immunol 2001; 31:2154) is another well studied oligonucleotide that induces high amounts of type I interferon in plasmacytoid dendritic cells.

The methods for synthesizing the oligonucleotide are well known for those skilled in the art and among others, solid-phase synthesis-is generally used. Specifically, in the process of the synthesis, the solid support used is controlled pore glass (CPG) bead. This bead has a surface with holes and channels and it is in these that the protected nucleotide is attached. The oligonucleotide synthesis begins with the 3'-most nucleotide and proceeds through a series of cycles composed of five steps that are repeated until the 5'-most nucleotide is attached. These steps are deprotection, activation, coupling, capping and stabilization.

Step 1. Deprotection

The protective group in the protected nucleoside attached to a CPG (controlled pore glass) bead is removed by trichloroacetic acid (TCA) leaving a reactive 5'-hydroxyl group.

Step 2. Activation

In this step, tetrazole attacks the coupling phosphoramidite nucleoside forming a tetrazolyl phosphoramidite intermediate.

Step 3. Coupling

The tetrazolyl phosphoramidite intermediate reacts with the hydroxyl group of the recipient and the 5' to 3' linkage is formed. The tetrazole is reconstituted and the process continues.

Step 4. Capping

In this step, an acetylating reagent composed of acetic anhydride and N-methyl imidazole is used to block a reactive hydroxyl group on its 5'-most end of the oligonucleotides to avoid of coupling failure.

Step 5. Stabilization

Once the capping step is accomplished, the last step in the cycle is oxidation step, which stabilizes the phosphate linkage between the growing oligonucleotide chain and the most recently added base. This step is carried out in the presence of Iodine as a mild oxidant in tetrahydrofuran (THF) and water.

Following this final step the cycle is repeated for each nucleotide in the sequence. After the completion of the synthesis, the single stranded DNA molecule is purified by methods such as HAP, PAGE, HPLC, C18 and OPC.

Example 2

Apoptosis of Human B-CLL Cells Induced by Oligo-2

1. Preparation of Human B-CLL Cells

Blood samples from untreated B-CLL (pathologically identified) patients (The First Hospital, Jilin University, China) were drawn after obtaining written informed consent approved. Peripheral blood mononuclear cells (PBMCs) were isolated by Ficoll-Paque (Pharmacia) density gradient centrifugation. CD5+CD19+CD23+B-CLL cells in PBMCs were purified using B-cell isolation kit (Miltenyi Biotec, Bergisch Gladbach, Germany) to >95% of CD5+CD19+CD23+ cells (B-CLL cells). The cell preparation was performed under the guidance of Miltenyi Biotec.

2. Apoptosis of Human B-CLL Cells Induced by Oligo-2

The B-CLL cells were incubated with Oligo 2 or 2006 or 2216 at a final concentration of 3 µg/ml in 10% human AB serum RPMI 1640 medium (HyClone) at $10^6$ cells/well in a 48-well plate. The Oligo 2, 2006 or 2216 were diluted in serum free RPMI 1640 medium (HyClone). An equal volume of the dilute (serum free RPMI 1640 medium (HyClone)) was used as a control (Medium).

Figure 1:
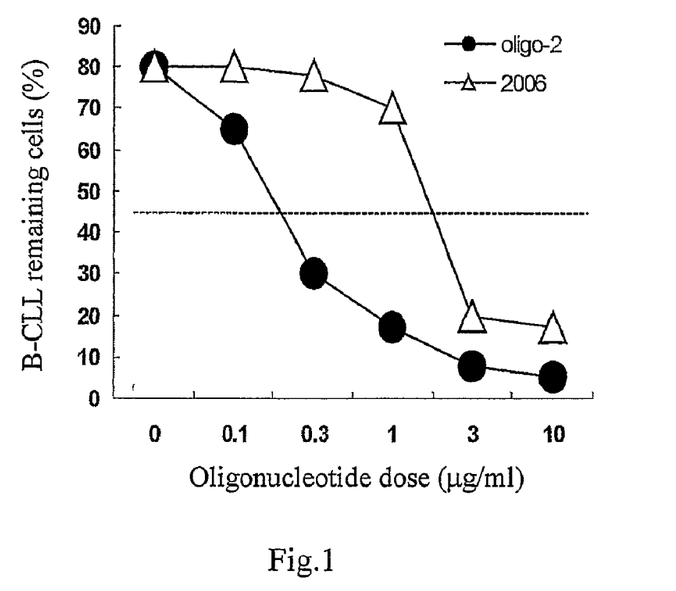
FIG. 1. Apoptosis of B-CLL Cells Induced by Oligo-2 (Dosage)

On day 3, 5 and 7 after incubation, the cells were counted and stained with tetramethyl-rhodamine ethylester (TMRE) (Molecular Probes Inc) (Lena Thyrell, et al. The Journal of Biological Chemistry Vol. 279, No. 23, Issue of June 4, pp. 24152-24162, 2004) for 10 minutes. The TMRE positive (viable) and TMRE-negative (apoptotic) B-CLL cells were determined by flow cytometry (B.D. FACS Aria). Viable B-CLL cell number was calculated by multiplying total cell count with the TMRE-positive cell percentage at each time point. The experiment was repeated with ten blood samples from B-CLL patients and the averaged result (n=10) showed that Oligo-2 significantly induced the apoptosis of B-CLL cells (Table-1) and the effect induced by Oligo-2 is approximately 2 fold stronger than that induced by 2006. In addition, the dose effect of Oligo-2 and 2006 on the apoptosis of the B-CLL cells was also observed. The result showed that that Oligo-2 at various dosages ranging from 0.1-10 µg/ml obviously induced the apoptosis of B-CLL cells (FIG. 1). Comparatively, at the dosage of 1 µg/ml, the apoptosis inducing effect of Oligo-2 is approximately 3-fold stronger than that of 2006. Together, these results demonstrate that Oligo-2 can be used to treat B-CLL by inducing the apoptosis of B-CLL cells.

TABLE 1

Apoptosis of B-CLL cells induced by Oligo-2 (Kinetics)
Viable B-CLL cells (%) (n = 10)

| Group | Time of Incubation (day) | | |
|---|---|---|---|
| | 3 | 5 | 7 |
| Medium | 82.2 ± 12.2 | 79.5 ± 9.25 | 81.3 ± 11.0 |
| 2216 | 67.7 ± 18.2 | 57.7 ± 16.7 | 50.7 ± 13.5 |
| 2006 | 66.5 ± 12.1 | 44.4 ± 15.0 | 40.2 ± 10.8 |
| Oligo 2 | 45.5 ± 9.5 | 17.6 ± 5.6 | 14.2 ± 3.1 |

Example 3

Up-Regulation of CD40 on Human B-CLL Cells by Oligo-2

1. Preparation of Human B-CLL Cells

Human B-CLL cells were isolated from B-CLL patients with the procedures as described as in example 2.

2. Up-Regulation of CD40 on Human B-CLL Cells by Oligo-2

The B-CLL cells were incubated with Oligo 2 or 2006 or 2216 at a final concentration of 3 µg/ml in 10% human AB serum RPMI 1640 medium (HyClone) at $10^6$ cells/well in a 48-well plate. The Oligo 2, 2006 or 2216 were diluted in serum free RPMI 1640 medium (HyClone). An equal volume of the dilute (serum free RPMI 1640 medium (HyClone)) was used as a control (Medium).

Figure 2:
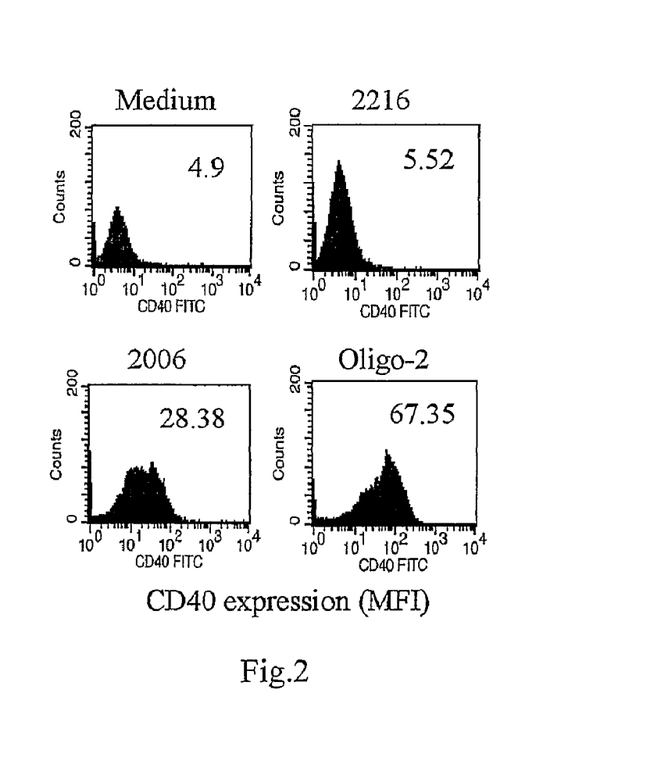
FIG. 2. The Effect of Oligo-2 on the Up-Regulation of CD40 on B-CLL Cells

On 7 day after the incubation, the cells were counted and stained with FITC-CD40 antibody (Becton ickinson) (Molecular Probes Inc) (Lena Thyrell, et al. The Journal of Biological Chemistry Vol. 279, No. 23, Issue of June 4, pp. 24152-24162, 2004) for 10 minutes. The CD40 antibody stained B-CLL cells were determined by flow cytometry (B.D. FACS Aria). The result (FIG. 2) showed that Oligo 2 significantly up-regulate the expression of CD40 on B-CLL cells, indicating that Oligo-2 can be used to treat B-CLL by up-regulating CD 40 on the cells. The up-regulation of CD 40 promotes the apoptosis of B-CLL cells, induces the growth inhibition of B-CLL cells and renders the B-CLL cells more immunogenic to stimulate the generation of CTLs specific to B-CLL cells. The experiment was repeated with at least ten blood samples from B-CLL patients with similar results.

Example 4

The Apoptosis of Human Small Lymphocytic Lymphoma Cells Induced by Oligo 2

1. Preparation of Human Small Lymphocytic Lymphoma Cells

The small lymphocytic lymphoma cells were isolated from the biopsy tissue of lymph node from patients (The First Hospital, Jilin University, China) with small lymphocytic lymphoma (pathologically identified) after obtaining written informed consent approved. The biopsy tissue was minced by rough surface glass slides to release the cells into 5 ml of 10% human AB serum RPMI 1640 media (HyClone) in a 6 cm culture plate. The released cells were filtered through stainless steel mesh and collected into a 50 ml conical tube containing 15 ml serum free RPMI 1640 medium (HyClone). The tube was centrifuged at 300×g for 10 minutes and then the supernatant was discarded. CD5+CD19+CD23+small lymphocytic lymphoma cells were purified using B-cell isolation kit (Miltenyi Biotec, Bergisch Gladbach, Germany) to >95% of CD5+CD19+CD23+cells (small lymphocytic lymphoma cells). The cell preparation was performed under the guidance of Miltenyi Biotec.

2. Apoptosis of Small Lymphocytic Lymphoma Cells Induced by Oligo-2

The small lymphocytic lymphoma cells were incubated with Oligo 2 or 2006 or 2216 at a final concentration of 3 µg/ml in 10% human AB serum RPMI 1640 medium (HyClone) at $10^6$ cells/well in a 48-well plate. The Oligo 2, 2006 or 2216 were diluted in serum free RPMI 1640 medium (HyClone). An equal volume of the dilute (serum free RPMI 1640 medium (HyClone)) was used as a control (Medium).

On day 3, 5 and 7 after the incubation, the cells were counted and stained with tetramethyl-rhodamine ethylester (TMRE) (Molecular Probes Inc)(Lena Thyrell, et al. THE JOURNAL OF BIOLOGICAL CHEMISTRY Vol. 279, No. 23, Issue of June 4, pp. 24152-24162, 2004) for 10 minutes. The TMRE positive (viable) and TMRE-negative (apoptotic) small lymphocytic lymphoma cells were determined by flow cytometry (B.D. FACS Aria). Viable small lymphocytic lymphoma cell number was calculated by multiplying total cell count with the TMRE-positive cell percentage at each time point. The experiment was repeated with five samples from the patients with small lymphocytic lymphoma and the averaged result (n=5) showed that Oligo-2 significantly induces the apoptosis of the small lymphocytic lymphoma cells (Table-2), indicating that Oligo-2 can be used to treat small lymphocytic lymphoma by inducing the apoptosis of small lymphocytic lymphoma cells.

TABLE 2

Apoptosis of small lymphocytic lymphoma cells induced by Oligo-2. Viable small lymphocytic lymphoma cells (%) n = 5

| Group | Time of Incubation (day) | | |
|---|---|---|---|
| | 3 | 5 | 7 |
| Medium | 81.2 ± 7.7 | 78.4 ± 9.1 | 77.1 ± 13.2 |
| 2216 | 68.5 ± 15.0 | 58.7 ± 12.3 | 52.1 ± 10.2 |
| 2006 | 67.6 ± 10.3 | 45.3 ± 8.9 | 41.1 ± 8.2 |
| Oligo 2 | 60.3 ± 12.2 | 23.2 ± 5.6 | 15.5 ± 6.2 |

Example 5

Up-Regulation of CD40 of Small Lymphocytic Lymphoma Cells Induced by Oligo 2

1. Preparation of Human Small Lymphocytic Lymphoma Cells

Human small lymphocytic lymphoma cells were isolated from patients with the procedures as described in example 4.

2. Up-Regulation of CD40 of Small Lymphocytic Lymphoma Cells Induced by Oligo-2

The small lymphocytic lymphoma cells were incubated with Oligo 2 or 2006 or 2216 at a final concentration of 3 μg/ml in 10% human AB serum RPMI 1640 medium (HyClone) at $10^6$ cells/well in a 48-well plate. The Oligo 2, 2006 or 2216 were diluted in serum free RPMI 1640 medium (HyClone). An equal volume of the dilute (serum free RPMI 1640 medium (HyClone)) was used as a control (Medium).

Figure 3:
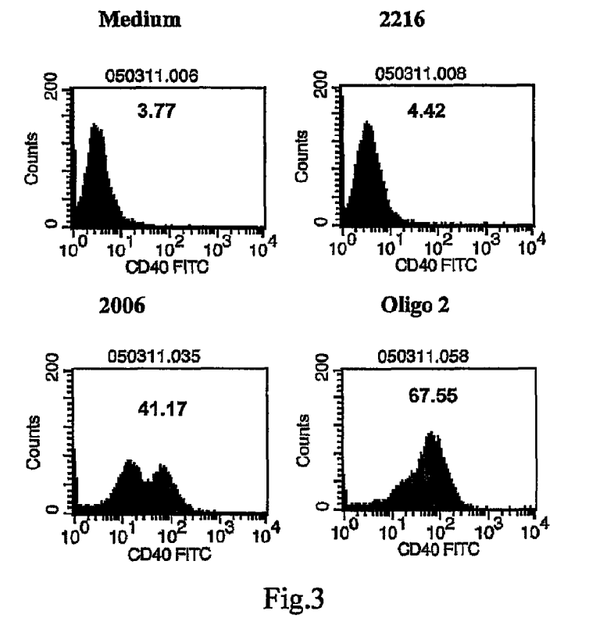
FIG. 3. The Effect of Oligo-2 on the Up-Regulation of CD40 on Small Lymphocytic Lymphoma Cells The small lymphocytic lymphoma cells were incubated with or without Oligo 2. On day 7, the cells were stained with FITC-CD40 antibody for analysis of CD40 expression using flow cytometry. The expression level was indicated with MFI number.

On day 7 after the incubation, the cells were counted and stained with FITC-CD40 antibody (Becton ickinson) (Molecular Probes Inc) (Lena Thyrell, et al. The Journal of Biological Chemistry Vol. 279, No. 23, Issue of June 4, pp. 24152-24162, 2004) for 10 minutes. The CD40 antibody stained small lymphocytic lymphoma cells were determined by flow cytometry (B.D. FACS Aria). The result (FIG. 3) showed that Oligo 2 significantly up-regulates the expression of CD40 on small lymphocytic lymphoma cells, indicating that Oligo-2 can be used to treat small lymphocytic lymphoma by up-regulating CD 40 on the cells. The up-regulation of the CD40 promotes the apoptosis of small lymphocytic lymphoma cells, induces the growth inhibition of small lymphocytic lymphoma cells and renders the small lymphocytic lymphoma cells more immunogenic to stimulate the generation of CTLs specific to the cells. The experiment was repeated with five samples with similar results.

Example 6

Apoptosis of Human B Cell-Acute Lymphoblastic/Lymphocytic Leukemia (B-ALL) Cells Induced by Oligo-2

1. Preparation of Human B-ALL Cells

Blood samples from untreated B-ALL (pathologically identified) patients (The First Hospital, Jlin University, China) were drawn after obtaining written informed consent approved. PBMCs were isolated by Ficoll-Paque (Pharmacia) density gradient centrifugation. CD19+CD10+B-ALL cells in PBMCs were purified using B-cell isolation kit (Miltenyi Biotec, Bergisch Gladbach, Germany) to >95% of CD19+CD10+cells (B-ALL cells). The cell preparation was performed under the guidance of Miltenyi Biotec.

2. Apoptosis of B-ALL Cells Induced by Oligo-2

The B-ALL cells were incubated with Oligo 2 or 2216 at a final concentration of 3 μg/ml in 10% human AB serum RPMI 1640 medium (HyClone) a at $10^6$ cells/well in a 48-well plate. The Oligo 2 or 2216 was diluted in serum free RPMI 1640 medium (HyClone). An equal volume of the dilute (serum free RPMI 1640 medium (HyClone)) was used as a control (Medium).

Figure 4:
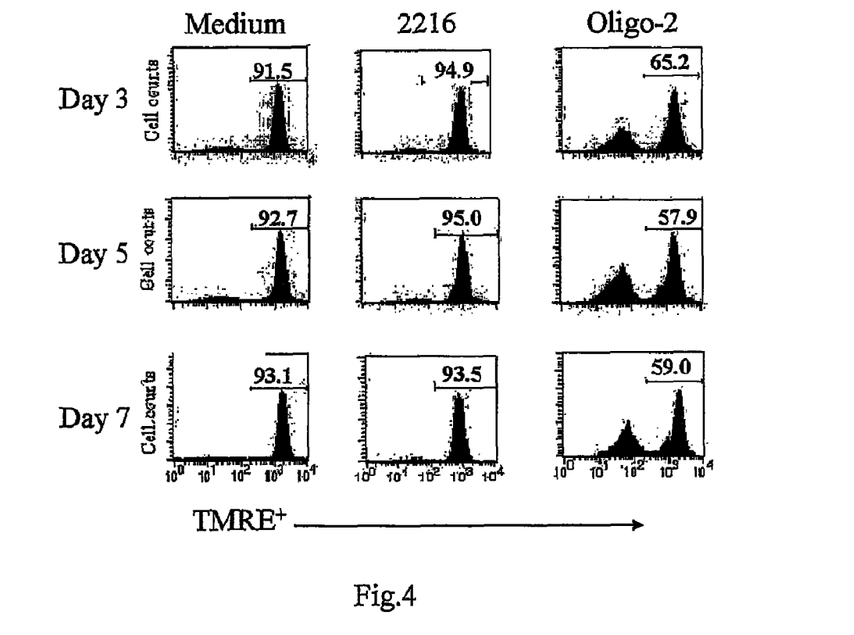
FIG. 4. Apoptosis of B-ALL Cells Induced by Oligo-2

On day 3, 5 and 7 after the incubation, the cells were counted and stained with tetramethyl-rhodamine ethylester (TMRE) (Molecular Probes Inc) (Lena Thyrell, et al. The Journal of Biological Chemistry Vol. 279, No. 23, Issue of June 4, pp. 24152-24162, 2004) for 10 minutes. The TMRE positive (viable) and TMRE-negative (apoptotic) B-ALL cells were determined by flow cytometry (B.D. FACS Aria). Viable B-ALL cell number was calculated by multiplying total cell count with the TMRE-positive cell percentage at each time point. The result showed that Oligo-2 significantly induced the apoptosis of B-ALL cells (FIG. 4), demonstrating that Oligo-2 can be used to treat B-ALL by inducing the apoptosis of B-ALL cells. The experiment was performed with ten blood samples from B-ALL patients with similar results.

Example 7

The Up-Regulation of Cb40 on B-ALL Cells by Oligo-2

1. Preparation of Human B-ALL Cells

Human B-ALL cells were prepared from the blood samples of patients with the procedures as described in example 6.

The B-ALL cells were incubated with Oligo 2 or 2216 at a final concentration of 3 μg/ml in 10% human AB serum RPMI 1640 medium (HyClone) a at $10^6$ cells/well in a 48-well plate. The Oligo 2 or 2216 was diluted in serum free RPMI 1640 medium (HyClone). An equal volume of the dilute (serum free RPMI 1640 medium (HyClone)) was used as a control (Medium).

Figure 5:
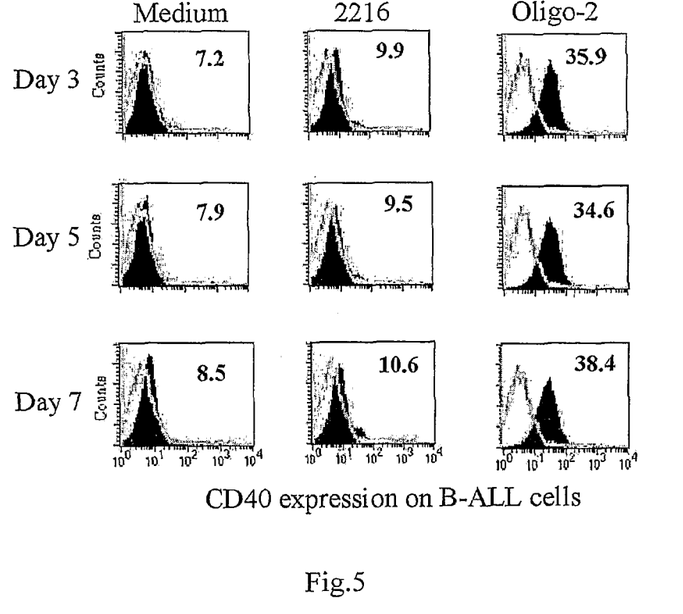
FIG. 5. Up-Regulation of CD40 on B-ALL Cells by Oligo 2

On day 3, 5, 7 after the incubation, the cells were counted and stained with FITC-CD40 antibody (Becton ickinson) (Molecular Probes Inc)(Lena Thyrell, et al. The Journal of Biological Chemistry Vol. 279, No. 23, Issue of June 4, pp. 24152-24162, 2004) for 10 minutes. The CD40 antibody stained B-ALL cells were determined by flow cytometry (B.D. FACS Aria). The result (FIG. 5) showed that Oligo 2 significantly up-regulate the expression of CD40 on B-ALL cells, indicating that Oligo-2 can be used to treat B-ALL by up-regulating CD 40 on the cells. The up-regulation of the CD40 promotes the apoptosis of B-ALL cells, induces the growth inhibition of B-ALL cells and renders the B-ALL cells more immunogenic to stimulate the generation of CTLs specific to B-ALL cells. The experiment was repeated with ten samples from the B-ALL patients with similar results.

Example 8

The Production of IL-10 from B-CLL Induced by Oligo 2

1. Preparation of Human B-CLL Cells

Human B-CLL cells were isolated from B-CLL patients with the procedures as described as in example 2.

2. The Production of IL-10 from B-CLL Induced by Oligo 2

Figure 6:
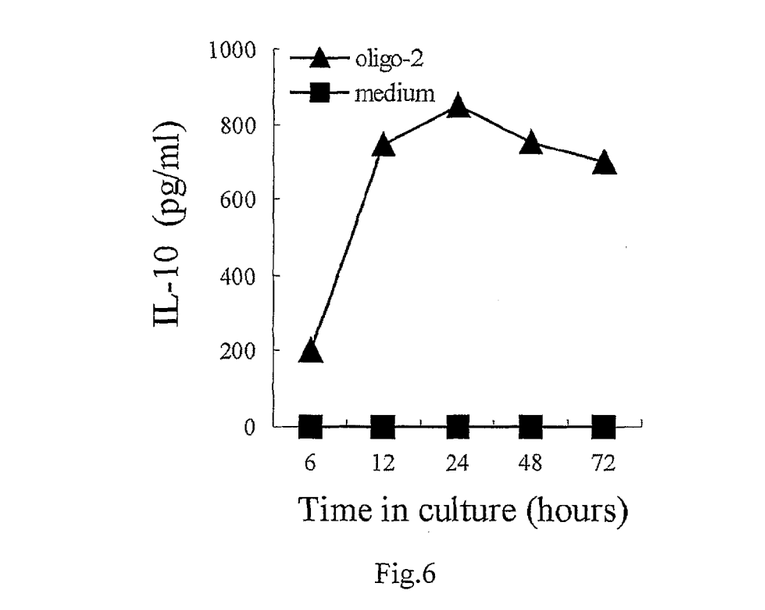
FIG. 6. Interleukin-10 Production from B-CLL Cells Induced by Oligo-2

The B-CLL cells were culture with Oligo 2 at a final concentration of 3 µg/ml in serum-free RPMI 1640 medium (HyClone) at at $10^6$ cells/well in a 48-well plate in triplicates. The Oligo 2 was diluted in serum free RPMI 1640 medium (HyClone). An equal volume of the dilute (serum free RPMI 1640 medium (HyClone)) was used as a control (Medium). The culture supernatants were collected at 72 h or the indicated time points and assessed for IL-10 in Fluorokine MAP Immunoarray (R&D Systems) system. Our data showed that triggering with Oligo-2 led to the production of a high level of IL-10 from B-CLL cells (FIG. 6). A profound increase of IL-10 production was detected at 6 h, peaked at 24 h, and remained high levels over the 72 h culture. In addition, our data further showed that adding exogenous rh-IL-10 (Schering Corp) into B-CLL cell cultures induced apoptotic B-CLL cells in an IL-10 dose-dependent manner, which could be specifically blocked by anti-IL-10 antibody (R & D Systems).

These findings demonstrate that Oligo-2 can be used to treat B-CLL by inducing the production of IL-10 that which provokes the apoptosis of B-CLL cells in an autocrine manner. The experiment was repeated by using at least ten samples of B-CLL patient.

Example 9

The Effect of Oligo-2 on the Proliferation of Human Normal PBMC

Human PBMCs were isolated from buffy coats of normal blood donors (The Blood Center of Jilin Province, China) by Ficoll-Hypaque density gradient centrifugation (Pharmacia). The viability of the PBMCs was 95-99% as determined by trypan blue exclusion.

Figure 7:
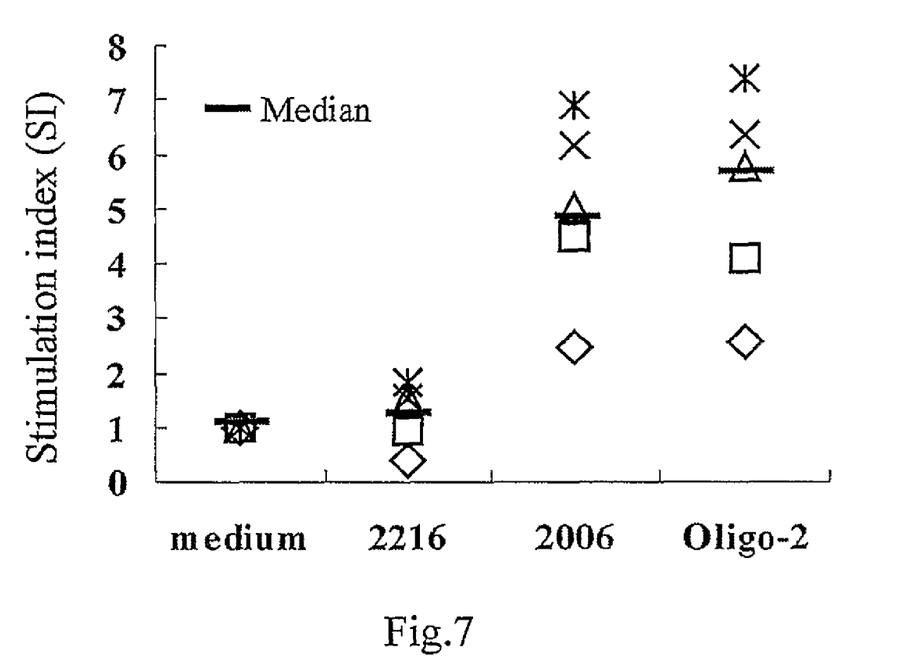
FIG. 7. The Effect of Oligo-2 on the Proliferation of Human Normal PBMC

The PBMCs ($6 \times 10^5$/well) were plated in 96-well U-bottomed plates (Costar) and cultured with or without the Oligo-2 (6 µg/ml) in triplicates for 36 h, followed by pulsing With [$^3$H] thymidine (New England Nuclear, Boston, Mass.) for 16 h. The cells were harvested on glass fiber filters and detected in a scintillation counter. The cell proliferation was expressed as SI (stimulation index) (from triplet wells). Data from five normal blood samples are shown. 2006 and 2216 were used in controls. The results showed that Oligo-2 could stimulate the PBMCs to proliferate obviously (FIG. 7), indicating that the Oligo-2, instead of inducing the apoptosis, is proliferation-stimulatory to normal human PBMCs and isn't toxic to the cultured cells.

Having described the invention in detail and by reference to the preferred embodiments it will be apparent to those skilled in the art that modifications and variations are possible without departing from the scope of the invention as defined in the following appended claims.

The invention claimed is:

1. A method for treating B cell neoplasm in a mammalian subject, comprising administering to a subject in need of treating a therapeutically effective amount of a pharmaceutical composition comprising an oligonucleotide having the sequence of SEQ ID NO: 1.

2. The method according to claim 1, wherein said method comprising inducing apoptosis of B-cell neoplastic cells.

3. The method according to claim 1, wherein said method comprising up-regulating CD40 on B-cell neoplastic cells.

4. The method according to claim 1, wherein said method comprising stimulating B-cell neoplastic cells to produce IL-10.

5. The method according to claim 1, wherein said B cell neoplasm is B cell leukemia, B cell lymphoma or myeloma.

6. The method according to claim 5, wherein said B cell leukemia is B cell chronic lymphocytic leukemia or B cell acute lymphocytic leukemia.

7. The method according to claim 5, wherein said B cell lymphoma is small lymphocytic lymphoma.

8. The method according to claim 1, wherein said mammalian subject is a human subject.

9. The method according to claim 1, wherein said pharmaceutical composition is administered enterally, parenterally or topically or by inhalation.

10. A method of inducing apoptosis of B-cell neoplastic cells, comprising contacting said B-cell neoplastic cells with a composition comprising an oligonucleotide having the sequence of SEQ ID NO: 1.

11. A method for enhancing the expression of CD40 on B cell neoplastic cells, comprising contacting said B-cell neoplastic cells with a composition comprising an oligonucleotide having the sequence of SEQ ID NO: 1.

12. A method for inducing B cell neoplastic cells to produce IL-10, comprising contacting said B-cell neoplastic cells with a composition comprising an oligonucleotide having the sequence of SEQ ID NO: 1.

13. The method according to any one of claims 10-12, wherein said B-cell neoplastic cells are B-cell chronic lymphocytic leukemia (B-CLL) cells.

14. The method according to claim 10 or 11, wherein said B-cell neoplastic cells are B-cell acute lymphocytic leukemia (B-ALL) cells.

15. The method according to claim 10 or 11, wherein said B-cell neoplastic cells are small lymphocytics lymphoma cells.

* * * * *